United States Patent [19]

Posner et al.

[11] Patent Number: 4,882,171

[45] Date of Patent: Nov. 21, 1989

[54] VANADIUM-PEROXIDE COMPOSITIONS AS INSULIN MIMICKERS

[76] Inventors: Barry I. Posner, 125 Geneva Crescent, Town of Mount Royal, Quebec, Canada, H3R 2A7; I. George Fantus, 4745 Meridian, Westmount, Canada, H3W 2C2

[21] Appl. No.: 105,212

[22] Filed: Oct. 7, 1987

[30] Foreign Application Priority Data

Oct. 16, 1986 [CA] Canada .................................. 520627

[51] Int. Cl.$^4$ ..................... A61K 33/24; A61K 33/40
[52] U.S. Cl. .................................... 424/616; 424/613; 424/646; 514/714; 514/866
[58] Field of Search ............... 424/130, 131, 616, 646; 514/714, 866

[56] References Cited

U.S. PATENT DOCUMENTS

| | | | |
|---|---|---|---|
| 4,143,080 | 3/1979 | Harders et al. | 436/66 |
| 4,295,853 | 10/1981 | Kasahara et al. | 436/66 |
| 4,343,794 | 8/1982 | Podos et al. | 424/131 |
| 4,361,487 | 11/1982 | Hills et al. | 423/571 |

OTHER PUBLICATIONS

S. Kadota et al., Abstract of ADA Meeting, Anaheim, Cal., on 23rd Jun. 1986; "Vanadate Augments Adipocyte IGF—2 Binding . . . ".
C. E. Heyliger, (1985), Science, vol. 227: pp. 1474–1477.
J. K. Klarluand, (1985), Cell, 41: 707–717.
Howarth and Hunt (1979), J. Chem. Soc. Dalton, pp. 1388–1391.

Primary Examiner—Dennis Albrecht
Attorney, Agent, or Firm—Bacon & Thomas

[57] ABSTRACT

A composition for use as an insulin mimic comprising substances containing:
(a) vanadate; and
(b) peroxide.

9 Claims, 3 Drawing Sheets

VANADIUM-PEROXIDE COMPOSITIONS AS INSULIN MIMICKERS

BACKGROUND OF THE INVENTION (i) Field of the Invention

This invention relates to a novel composition for use as an insulin mimic comprising peroxide and vanadate. The mimic can produce insulin effects in the absence of insulin.

(ii) Description of the prior art

Since the discovery of insulin there has been a treatment for diabetes mellitus. In about 85% of cases insulin deficiency is not significant; rather there is a resistance in tissues to the effectiveness of the insulin. Oral hypoglycemic agents have been developed, in tablet and capsule form, to treat diabetes mellitus. These agents have been used to replace insulin in the type of disease where there is no severe deficiency of insulin. They act primarily by stimulating increased insulin production from the pancreas, though some appear to influence the peripheral action of insulin.

Insulin acts initially by binding to its receptor site in target tissues. The receptor consists of a portion which binds the insulin molecule and another portion which initiates the biologic response. This latter has been shown to be a protein kinase. Insulin binds to its receptor and activates the protein kinase which then changes the cellular milieu and thus leads to the characteristic responses to insulin.

It is known that vanadate alone is a weak mimicker of insulin action probably through increasing the protein kinase activity, see "Vanadate Augments Adipocyte IGF-2 binding in a manner similar but not identical to insulin" by S. Kadota et al., (abstract presented at the American Diabetes Association Meeting in Anaheim, Calif. on 23rd June 1986). (IGF stands for insulin growth factor). In the same abstract it was disclosed that 1mM $H_2O_2$ markedly augmented the effect of vanadate in promoting the translocation of IGF receptors from within the fat cell to the cell surface. This is based on the observation that vanadate $+H_2O_2$ (1mM) increased the cell surface binding of $^{125}I$-IGF-2 by 199% over that produced by vanadate alone.

In addition, vanadate has been put in the drinking water of diabetic rats and has been shown to lower blood glucose and to improve cardiac performance in these animals (C.E. Heyliger (1985), Science, Vol. 227: p. 1474–1477). Thus there are data in the literature pointing to applicability of some form of vanadate.

It has now been found that vanadate and peroxide, when mixed together, are potently synergistic in producing an insulin effect. Furthermore, this combination produces an intense stimulation of the receptor's protein kinase. It has recently been found that the combination works because peroxide alters the vanadate to produce a peroxide of vanadate which is many times more potent than the original vanadate and even more potent than maximal doses of insulin in producing an insulin-like effect. The possibility is envisaged that this simple yet very powerful compound has clinical application in the treatment of diabetes mellitus, both the insulin deficient kind and that in which there is tissue resistance to the action of insulin. It represents a new class of agent capable of bypassing the insulin binding site and chemically activating the receptor's protein kinase independently of the ambient levels of insulin. To date there is no known pharmacological agent which can "turn on" the insulin receptor protein kinase to produce insulin effects in the absence of insulin.

SUMMARY OF THE INVENTION

The invention therefore provides compositions for use as insulin mimics comprising pharmaceutically acceptable substances providing both:

(a) vanadate; and (b) peroxide.

An advantage of the present invention is that the peroxide of vanadate is much more powerful than vanadate and thus can be used at much lower concentrations of the metal. This reduces toxicity which is known to result from inappropriate quantities of vanadate, (J. K. Klarlund, (1985) Cell, 41: 707–717).

The term "vanadate" is intended to mean vanadium in its V+ oxidation state combined with oxygen in physiologically acceptable solution. As such, the term may include, for example $VO_4^{3-}$ (orthovanadate) and $VO_3^-$ (metavanadate).

The term peroxide is intended to include any oxidising agent able to combine with vanadate to form the insulin mimic according to the invention. As such, the preferred peroxides are, for example, t-butylhydroperoxide, benzoyl peroxide, m-chloroperoxibenzoic acid, cumene hydroperoxide, peracetic acid, hydroperoxilinoleic acid, hydroperoxiarachidonic acid, ethyl peroxide, pyridine peroxide and hydrogen peroxide.

In the following discourse reference is made to "tyrosine kinase activity". Tyrosine kinase or tyrosine specific protein kinase is the same as insulin receptor kinase and was referred to at the beginning of this text simply as "protein kinase".

The active product according to the present invention, is prepared by mixing vanadate and peroxide together optionally in a buffer, preferably at neutral pH and preferably at room temperature. It is preferred to use an alkali earth metal or alkali metal vanadate eg. sodium. As peroxides, hydrogen peroxide is most preferred. The reaction occurs spontaneously under these conditions to form substances which are oxo-complexes of vanadium or pervanadates (peroxides of vanadate). These complexes have been studied and documented by Howarth and Hunt [J. Chem. Soc. Dalton (1979) p 1388 –1391] and at least 8 to 11 oxocomplexes have been distinguished by NMR spectroscopy.

In one embodiment of the present invention where the source of peroxide is hydrogen peroxide, simple mixing of $H_2O_2$ and vanadate at a range of concentrations produces the active compound(s). With $H_2O_2$ the preferred concentration ranges from $10^{-1}$ to 10mM with 1mM most preferred. The vanadate concentration ranges preferably from $1 \times 10^{-4}$ to 10mM, but most preferably from $10^{-3}$ to 1mM, see FIG. 2. That the results depend on oxo-complex formation is confirmed in this embodiment by removal of $H_2O_2$ with catalase and subsequent observation of continuing biological activity greater than that generated by equivalent concentrations of vanadate alone.

BRIEF DESCRIPTION OF THE DRAWINGS

FIG. 1 shows two bar charts comparing IGF-2 binding with tyrosine kinase activity when certain insulin mimics are added to rat adipocytes.

DETAILED DESCRIPTION OF THE INVENTION

As discussed above, the characteristic effects of insulin are known to be an augmentation of IGF-2 binding (to fat and liver cell surfaces) and an increase in tyrosine kinase activity in those cells. Furthermore, insulin stimulates lipogenesis (i.e. synthesis of fats) and inhibits lipolysis (i.e. breakdown of triglyceride) as well as acting as an ahabolic agent (i.e. stimulator of protein synthesis).

All these properties are exhibited by the novel pervanadates according to the present invention and are supported respectively by the following examples.

In the examples, the effect of pervanadate is compared to the effect of known insulin mimics such as vanadate alone and hydrogen peroxide alone. Comparison is also made with insulin itself.

Example 1

In a comparative test, to show IGF-2 binding to the cell surface, rat adipocytes were preincubated with insulin (10ng/ml), vanadate (1mM) and/or $H_2O_2$ (1mM) for 15 minutes at 37° C., and the binding of $^{125}I$-IGF-2 was determined. The results of this test are shown in Table I. Data are expressed as a percent of amount of binding in the control in which $^{125}I$-IGF-2 alone is incubated with the cells.

TABLE 1

| Additions | % of control |
|---|---|
| Insulin (I) | 289 ± 16 |
| $H_2O_2$ (H) | 138 ± 12 |
| Insulin + $H_2O_2$ (I + H) | 230 ± 12 |
| Vanadate (V) | 172 ± 10 |
| Vanadate + $H_2O_2$ (V + H) | 488 ± 23 |

The results are shown graphically in the lower part of FIG. 1.

The upper part of FIG. 1 graphically illustrates the action of the same additions on tyrosine kinase activity.

Example 2

Figure 7:
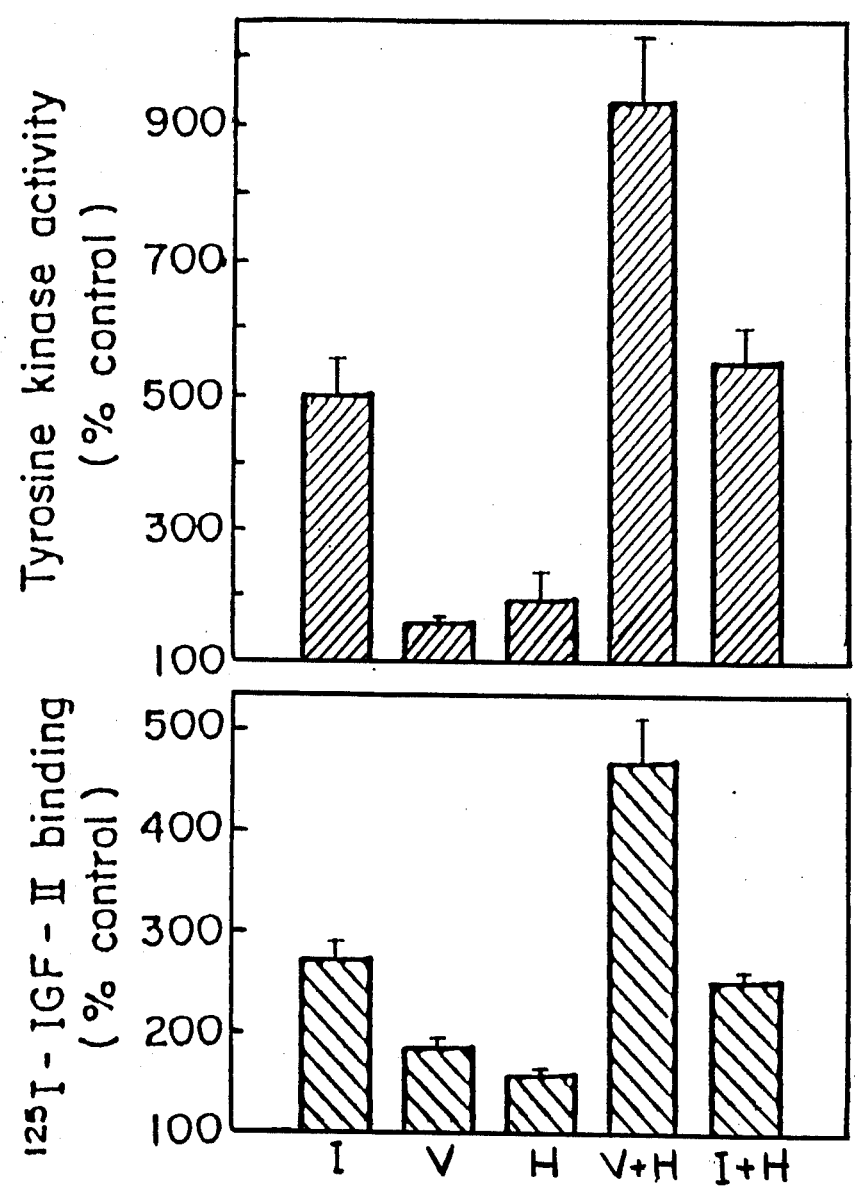
Figure 2:
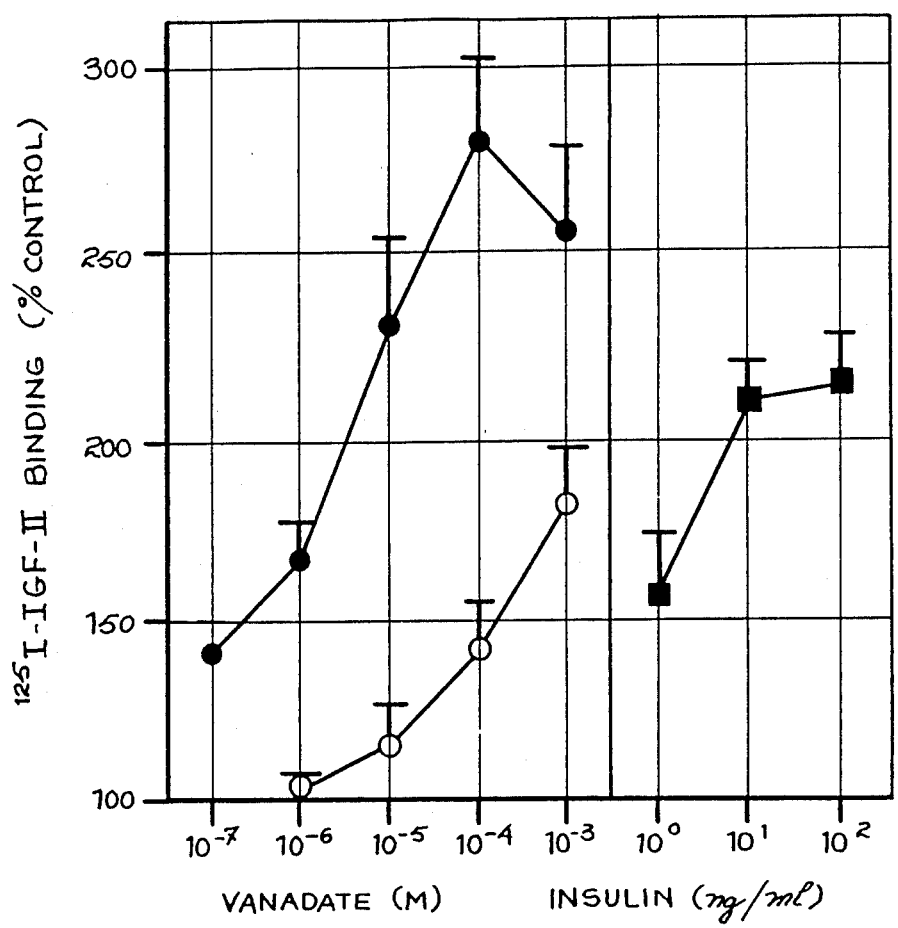
FIG. 2 shows the action of different doses of vanadate with or without peroxide on the binding of labelled IGF-2 to rat adipocytes compared to the action of other additives.

A second experiment, the results of which are illustrated in FIG. 2, shows the effect of different doses of vanadate on the binding of I-125 labelled IGF-II to rat adipocytes.

Determination of $^{125}I$-IGF-II binding (shown in FIG. 2) is achieved by incubating adipocytes with vanadate (white circles on Figure); hydrogen peroxide (1mM) plus vanadate (black circles); and insulin (black squares) for 15 minutes at 37 C. Each value shown is the mean ± S.E. (Standard Error) of three separate experiments.

FIG. 2 demonstrates that whereas vanadate alone has an effect over a dose range as indicated, the effect of vanadate plus peroxide is much more potent. This is indicated by its efficacy at much lower concentrations of vanadate plus $H_2O_2$ compared to vanadate alone, and by its greater maximal effect even greater than that of maximal concentrations of insulin (shown alongside).

In this example, vanadate alone produced biological effects in the range from $1 \times 10^{-1}$ to 1.0 mM. The maximal effect achieved (with vanadate alone) was about 60% that seen with maximal doses of insulin. In contrast the oxo-complex(es) according to the invention showed biological activity over the range of $1 \times 10^{-4}$ (vanadate concentration) with maximal effects observed at $1 \times 10^{-1}$mM. The maximal effect observed was 1.5-3 fold that seen with maximal doses of insulin.

Example 3

Figure 3:
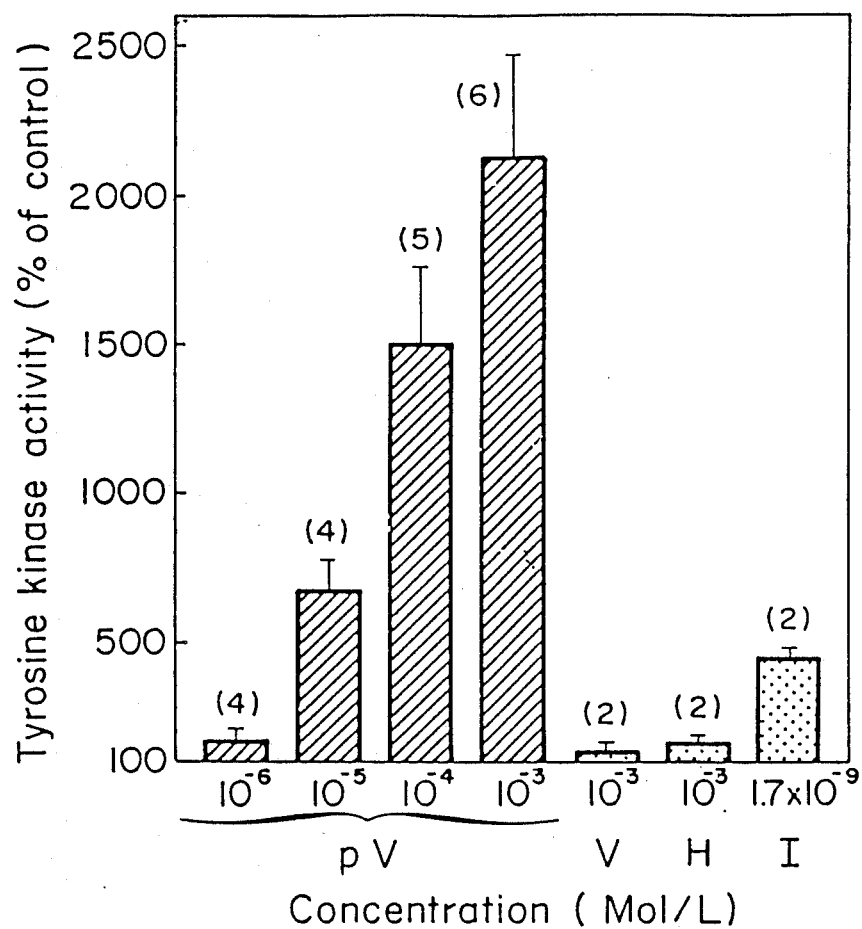
FIG. 3 shows tyrosine kinase activity in adipocytes resulting from various concentrations of pervanadate.

In this example, the effect of pervanadate (pV) added to adipocytes on insulin receptor tyrosine kinase activation was evaluated. The combination of different concentrations of vanadate with $H_2O_2$ ($10^{-3}$M) for 15 min prior to catalase addition produced a powerful dose-dependent activation of wheat germ agglutinin—purified tyrosine kinase as measured by $^{32}p$ incorporation into the synthetic substrate poly (Glu, Tyr) (4:1) (FIG. 3). At the vanadate ($10^{-4}$M) plus $H_2O_2$ ($10^{-3}$M) concentration which maximally stimulated IGF-II binding, (see FIG. 2) tyrosine kinase activity was 1400% above control, whereas vanadate ($10^{-3}$M) alone (V), $H_2O_2$ ($10^{-3}$M) alone (H) and insulin (10 ng/ml) alone (I) augmented kinase activity by only 32,58 and 349% over control respectively. These results are reproduced graphically in FIG. 3.

Example 4

In a test using rat adipocytes to establish the effect of vanadate (V) with hydrogen peroxide (H) on lipogenesis and lipolysis, it was established that concentrations of vanadate of $10^{-7}$ M with hydrogen peroxide of $10^{-3}$ M augmented lipogenesis to an extent equal to the effect of vanadate alone at a concentration of $10^{-4}$M. Vanadate at $10^{-5}$M with hydrogen peroxide at $10^{-3}$M inhibited lipolysis maximally as did vanadate alone but at higher concentration i.e. $10^{-3}$M. Catalase added to vanadate with hydrogen peroxide at zero but not 15 minutes after mixing, abolished synergism indicating that the active compound is a peroxide of vanadate. Thus the potency of pervanadate as an insulin mimetic exceeds that of vanadate alone by a factor of between 100 and 1000 in respect of these activities.

Example 5

In this example, the effects of pervanadate on protein synthesis in adipocytes were investigated.

Adipocytes were isolated by collagenase digestion and protein synthesis was assessed by the incorporation 3,4,5-$^3$H-leucine (0.5 uCi/ml) over 1 h at 37° C. into trichloroacetic acid (10%) precipitable material.

Cells ($2-3 \times 10^5$/ml) were incubated for 2 h at 37° C. in the presence or absence of insulin $10^{-10}$ and $10^{-7}$ M, Vanadate 2 uM, 10 uM, 50uM and 100uM, $H_2O_2$ 100 uM, and pervanadate 2 uM, 10uM, 50uM and 100uM. This was followed by a 1 h incubation with radiolabelled leucine. The reaction was terminated by the addition of cold TCA and centrifugation. The pellet was counted in a beta counter. The results are given in Table 2.

TABLE 2

| | Leucine Incorp % (% of control ± S.E.) | No of Expts. carried out |
|---|---|---|
| Control | 100 | 6 |
| I $10^{-10}$M | 119 ± 4.7 | 6 |
| $10^{-7}$M | 136 ± 5.5 | 6 |
| V 2 uM | 101 ± 5.0 | 2 |
| 10 uM | 104 ± 3.5 | 6 |
| 50 uM | 105 ± 6.0 | 5 |
| 100 uM | 107 ± 8.0 | 5 |
| pV 2 uM | 123 ± 1.0 | 2 |
| 10 uM | 122 ± 5.3 | 6 |

TABLE 2-continued

| | Leucine Incorp % (% of control ± S.E.) | No of Expts. carried out |
|---|---|---|
| 50 uM | 117 ± 5.0 | 5 |
| 100 uM | 108 ± 6.9 | 4 |
| H$_2$O$_2$ | 105 ± 4.7 | 5 |

As can be seen from the results in Table 2, pervanadate stimulates protein synthesis at low concentrations (1 uM) to at least 50% of maximal insulin but inhibits at higher concentrations (50-100 uM). Vanadate alone does not significantly stimulate leucine incorporation.

Example 6A

In live rat studies vanadate (sodium salt) and the reaction mixture (phosphate-buffered saline containing vanadate and H$_2$O$_2$ at neutral pH) was injected into 200 g rats via the internal jugular vein. Vanadate (0.2 to 0.4 ml of 1 mM solution) had no effect whereas 0.2 to 0.4 ml of the vanadate H$_2$O$_2$ mixture (vanadate 1mM; H$_2$O$_2$,1mM) resulted in a decrease of blood glucose from 30 to 40%. This decrease was short-lived.

Example 6B

In a further experiment to determine the effect of pervanadate on lowering blood sugar in intact rats, male Sprague-Dawley rats weighing 160-200 g were anesthetized with intraperitoneal pentobarbital (15 mg per 200 g b wt). Solutions were injected into the jugular vein and blood samples were removed for determination of blood sugar by a standard glucose oxidase procedure. In five different animals the administration of b 0.5 ml of 2 mM vanadate plus 2 mM hydrogen peroxide resulted in a decrease in blood sugar of 29±5% (mean ± S.E., n=5) by 60 to 90 minutes post injection. In contrast the injection of 0.5 ml of 2mM vanadate had no effect at all in lowering blood sugar.

These data (Examples 6A and 6B) suggest that the insulin-like effects of pervanadate seen in incubation with adipocytes can also be observed in the intact mammal. Thus a method of reducing blood sugar and a method for treatment of hyperglycemia are suggested.

Example 7

The present inventors also very recently demonstrated that pervanadate, according to the present invention, is a potent activator of the insulin receptor kinase in cultured hepatocytes. Thus the insulin-like effects are not restricted to the fat cell but are demonstrable in another important target organ for insulin, namely, the liver. The effect on the liver insulin-receptor kinase is very comparable to that seen with the fat cell and stimulation is seen over the same range of concentrations.

What is claimed is:

1. A method of augmenting protein synthesis comprising addition of an effective amount of a composition comprising vanadate in a concentration range of from $10^{-4}$ to 10 millimolar and of peroxide in a concentration range of from $10^{-1}$ to 10 millimolar to an environment in which protein synthesis takes place.

2. A method according to claim 1, wherein the peroxide is hydrogen peroxide.

3. A method according to claim 2, wherein the concentration of peroxide is 1mM.

4. A method according to claim 3, wherein the vanadate is in the form of sodium vanadate.

5. A method according to claim 1, wherein the concentration of vanadate ranges from $10^{-3}$ to 1mM.

6. A method according to claim 5, wherein the peroxide is hydrogen peroxide.

7. A method according to claim 1, wherein the vanadate is an alkaline earth metal or alkali metal vanadate.

8. A method according to claim 7, wherein the peroxide is selected from the group consisting of t-butylhydroperoxide, benzoyl peroxide, m-chloroperoxibenzoic acid, cumeme hydroperoxide, peracetic acid, hydroperoxilinoleic acid, hydroperoxiarachidonic acid, ethyl peroxide, pyridine peroxide and hydrogen peroxide.

9. A method according to claim 7, wherein the peroxide is hydrogen peroxide.

* * * * *